United States Patent [19]
Goodrich

[11] Patent Number: 5,387,203
[45] Date of Patent: Feb. 7, 1995

[54] SUBCUTANEOUS EXTRACTOR

[76] Inventor: Hubert J. Goodrich, 3313 Westleigh Ave., Las Vegas, Nev. 89102

[21] Appl. No.: 83,446

[22] Filed: Jun. 28, 1993

[51] Int. Cl.$^6$ .............................................. A61M 1/00
[52] U.S. Cl. .................. 604/313; 604/314; 604/316; 604/46
[58] Field of Search .............. 604/46, 48, 73, 181, 604/289, 313, 316, 314, 315; 606/167, 181, 184, 185, 171

[56] References Cited

U.S. PATENT DOCUMENTS

| | | | |
|---|---|---|---|
| 1,221,103 | 4/1917 | Sorensen | 604/316 |
| 2,360,051 | 10/1941 | Eweson | 128/297 |
| 3,068,868 | 12/1962 | Skopyk | 604/316 |
| 3,623,475 | 11/1971 | Sanz et al. | 604/46 |
| 3,683,922 | 8/1972 | Cutter | 604/314 |
| 3,742,954 | 7/1973 | Strickland | 128/302 |
| 3,896,810 | 7/1975 | Akiyama | 604/316 |

FOREIGN PATENT DOCUMENTS

| | | | |
|---|---|---|---|
| 0670171 | 11/1929 | France | 604/313 |
| 1238616 | 4/1967 | Germany | 604/313 |

*Primary Examiner*—Paul Prebilic

[57] ABSTRACT

A device for extracting pus, blood and other materials from beneath the skin. The device is made of a clear plastic tube open at both ends (10). One end is placed over the skin which has material to be extracted. The other end contains a plunger device (16) which creates a vacuum in the tube when it is withdrawn from the tube. As the vacuum pressure increases, the skin and underlying material are drawn into the tube until it is penetrated by a recessed piercing device (14) which is attached to an extrusion (12) approximately in the center of the tube (10). After being pierced, the underlying material is drawn from beneath the skin to the surface.

2 Claims, 1 Drawing Sheet

SUBCUTANEOUS EXTRACTOR

BACKGROUND-FIELD OF INVENTION

This invention relates to the removal of pus, blood and other material from beneath the skin and more particularly a device for piercing the skin and extracting fluids and other material which occur in or beneath the skin.

Background-Description of Prior Art

People and animals often have deposits of body fluids and other material in or beneath their skin. Body fluids include blood, and other fluids. Material includes pus and other substances. Usually the deposit appears in the form of a pimple, boil, abscess, carbuncle, or pustule. Traditional procedures for removing the unwanted material from these areas includes squeezing, or piercing followed by squeezing.

For example, squeezing the pimple between the fingers works when the pimple consists of a well defined pus sac which occurs just beneath the skin. Although the pus can be removed, the squeezing action compresses and often damages the flesh surrounding the pimple.

Lancing followed by squeezing works when the pimple consists of a pus sac which is less well defined or because it is located deeper below the skin. Lancing contains the inherent danger of lancing too far through the pus sac thereby causing unnecessary bleeding and possibly spreading infection.

A lance such as a needle or other sharp tool, when used around delicate areas such as the eyes, may do serious damage if it is mishandled in any way. Before penetrating the skin, pressure must be applied to the lance which then compresses the underlying skin and tissue. This pressure coupled with the rapid penetration of the lance often causes pain and discomfort to the bearer of the pimple.

Squeezing, after lancing, usually requires less pressure because there is an open path to the outside. However, squeezing the pus or other matter may still be a difficult task depending on the depth and/or location of the unwanted material. For example if the pus sac is located on one of the eyelids, or near the eye or behind the ear it would be difficult to squeeze it out even if the sac was first lanced.

Objects and Advantages

Accordingly, several objects and advantages of my invention are:
  (a) to provide a simple, effective, inexpensive and easily operated device which can be used by the general public to remove unwanted fluids and material from beneath the skin.
  (b) to provide a device which will enable the operator to lance the skin with a piercing device that is safely recessed away from the skin so that damage will be minimized if the device is mishandled.
  (c) to provide a device which will allow the operator to directly observe and control the penetration of the piercing device.
  (d) to provide a device which will suction the unwanted material out of the underlying tissue so that no squeezing is necessary and no unnecessary damage is done to the surrounding tissue.

Further objects and advantages are to provide a device that will draw any type of fluid or material from tissue while minimizing the amount of pain and damage to the surrounding tissue. Still further objects and advantages will become apparent from a consideration of the ensuing description and drawings.

DRAWING FIGURES

Figure 1:
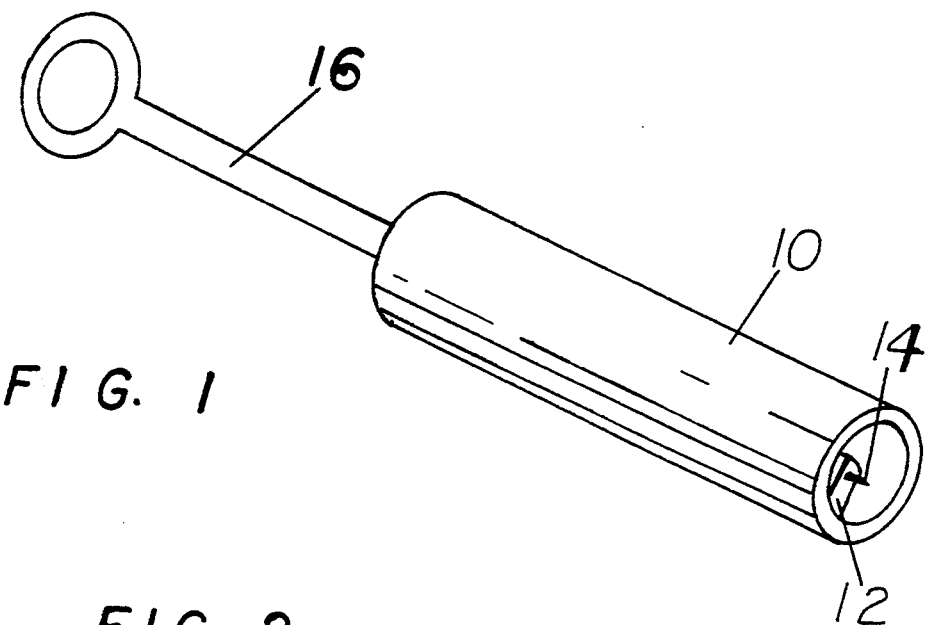
FIG. 1 is a perspective view of a subcutaneous extractor.
Figure 2:
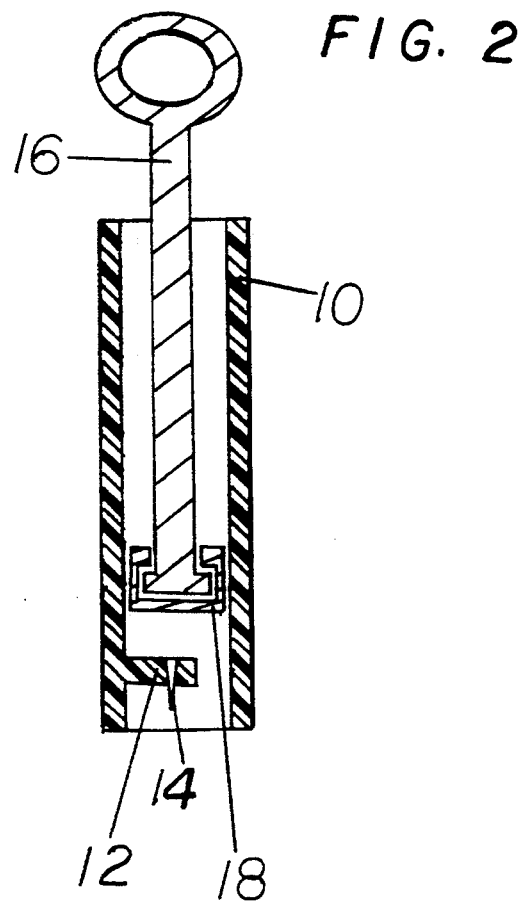
FIG. 2 is a longitudinal cross sectional view of a subcutaneous extractor.
Figure 3:
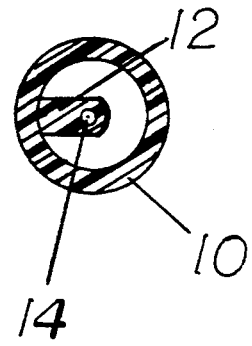
FIG. 3 is a cross sectional view of the tubular housing of the subcutaneous extractor.

REFERENCE NUMERALS IN DRAWINGS 10 tubular shaped housing
12 extrusion from housing
14 piercing device
16 plunger device with finger hole
18 seal Description-FIGS. 1 to 3

A typical embodiment of the present invention is illustrated in FIG. 1 and FIG. 2. A tube shaped housing 10 constructed of a clear material such as polyethylene or other material which will allow the operator of the subcutaneous extractor to view the tissue being pierced; the wall of the tubular housing 10 must be of sufficient thickness and strength so that it does not collapse when a partial vacuum is created in the housing 10.

As shown in FIG. 2 the bottom end of the housing 10, the end closest to the piercing device 14, is smooth. This can be accomplished through the extrusion process, sanding, planing or any other smoothing process.

In the present embodiment an extrusion 12 from the housing is used to secure and position a piercing device 14.

The piercing or cutting device 14 will consist of a material which is capable of being sharpened to a fine point or edge, such as stainless steel or any other metal or material which can be sharpened.

A plunger device 16 is located in the housing 10. The end of the plunger device 16 which is outside of the housing has a finger ring. The other end of the plunger device 16 is enlarged. The plunger device 16 can be made by the extrusion process. Polyethylene or any other material which is strong enough to withstand the pressures of creating a partial vacuum can be used to make the plunger (a source of variable negative pressure) 16.

A seal 18 made of rubber, plastic, or any other material having rubber-like properties will be formed into a shape which can fit over the enlarged end of the plunger 16 which is inside the housing 10. The portion of the seal which is between the plunger 16 and the housing 10 must be thick enough to touch and exert a pressure on the plunger 16 and the inside surface of the housing 10.

Operation-FIGS. 1, 2, 3

To use the subcutaneous extractor to remove pus and other liquids from a pimple, push the plunger device 16 into the the housing 10 until it is near the extrusion 12 from the housing 10. Press the open end of the tubular housing 10 lightly onto the skin where it is approximately centered above the pimple. Begin withdrawing the plunger device 16 with the finger ring. This will cause a partial vacuum to occur in the tubular housing 10 between the seal 18 and the skin. As the plunger device 16 is withdrawn further the partial vacuum pressure will increase and the skin and pimple will be drawn into the housing 10 towards the piercing device 14.

Because the housing 10 is clear the operator can directly see if the piercing device 14 is located in an appropriate position above the pimple. If not, then the plunger device 16 can be depressed and the housing 10 can be placed in a more appropriate location above the pimple.

Once the skin and pimple are drawn into the housing 10 just beneath the piercing device the operator, through the use of the plunger device 16 can increase the partial vacuum just enough to pierce the skin and pimple sac. Therefore the depth of the puncture can be accurately controlled by the operator observing the meeting of the pimple and the piercing device 14.

After the pimple sac has been pierced the contents will be drawn outside of the skin into the partial vacuum in the housing 10. The subcutaneous extractor can then be removed. The unwanted contents of the pimple can then be wiped off of the skin.

Summary, Ramifications, and Scope

Accordingly, the reader will see that the subcutaneous extractor can be used to remove materials such as pus, blood, other liquids, and materials that occur beneath the skin. The subcutaneous extractor has the advantages over squeezing or piercing followed by squeezing in that:

the piercing device is recessed in the housing and an inadvertent slip by the operator would not cause serious damage to delicate parts of the body; and by controlling the vacuum pressure and directly observing the meeting of the piercing device and the skin the operator can control and minimize the penetration of the piercing device thereby avoiding overpenetration; and at the instant of piercing, the skin is stretched and therefore the damage done to skin by the piercing device 14 is minimized; and at the instant of piercing the skin is stretched and the amount of pain caused by the piercing device 14 is minimized because there are fewer nerves per square centimeter of stretched skin; and after piercing, the material to be removed from under the skin will be suctioned into the partial vacuum and therefore no damage to the surrounding tissue is caused by squeezing; and the subcutaneous extractor can be used on parts of the body where it is difficult or next to impossible to squeeze by hand.

Although the description above contains many specificities, these should not be construed as limiting the scope of the invention but as merely providing illustrations of some of the presently preferred embodiments of this invention. For example, the cylindrical shaped housing could have finger rings on the sides so that it could be operated easily with one hand; and the piercing device could be attached in such a way that it could be easily replaced after each use; and instead of the bottom of the housing having a circular shape it could be some other shape to facilitate use on different parts of the body; and the piercing device could be spring loaded to facilitate piercing.

Thus the scope of the invention should be determined by the appended claims and their legal equivalents, rather than by the examples given.

I claim:

1. A device for removing pus, blood and other materials from in and beneath the skin comprising:
    (a) a housing of sufficient thickness and strength so that it does not collapse when a partial vacuum is created in the housing and has an opening at the bottom, and
    (b) a means for creating variable negative pressure in the housing, said means capable of creating negative pressure of sufficient strength to draw skin into the housing through the bottom opening
    (c) a piercing means fixedly secured within the housing with said piercing means recessed above the bottom opening of said vacuum chamber approximately in the center, said piercing means recessed from the bottom opening such that skin drawn into the housing can be pierced by a fine point or edge of the piercing means such that the skin is stretched to the extent that damage done to the skin by the piercing means is minimized whereby an operator of said device can place the bottom opening of said housing over skin which has material to be removed underneath and by controlling the negative pressure the operator can increase the vacuum pressure to draw the underlying skin into said housing where the skin is pierced by said piercing means and the material to be removed from beneath the skin is extracted into said housing.

2. The device of claim 1 wherein said housing being made of a clear material whereby the operator can directly observe the extraction of the material to be removed and therefore can control the strength of negative pressure to apply a minimum amount of vacuum pressure necessary for said piercing means to pierce the skin and underlying tissue to a minimum depth necessary to extract the material to be removed.

* * * * *